United States Patent [19]

Mitchell et al.

[11] Patent Number: 5,569,783
[45] Date of Patent: Oct. 29, 1996

[54] VICARIOUS NUCLEOPHILIC SUBSTITUTION TO PREPARE 1,3-DIAMINO-2,4,6-TRINITROBENZENE OR 1,3,5-TRIAMINO-2,4,6-TRINITROBENZENE

[75] Inventors: Alexander R. Mitchell; Philip F. Pagoria; Robert D. Schmidt, all of Livermore, Calif.

[73] Assignee: The Regents of the University of California, Oakland, Calif.

[21] Appl. No.: 440,017

[22] Filed: May 12, 1995

[51] Int. Cl.⁶ ................................................. C07C 45/00
[52] U.S. Cl. ............................................ 74/395; 564/441
[58] Field of Search ................................. 564/395, 441; 568/932, 933, 934

[56] References Cited

U.S. PATENT DOCUMENTS

| | | | |
|---|---|---|---|
| H1078 | 7/1992 | Norris et al. | 548/126 |
| H1304 | 4/1994 | Norris et al. | 548/126 |
| 4,032,377 | 6/1977 | Benziger | 149/105 |
| 4,248,798 | 2/1981 | Atkins | 564/441 |
| 4,952,733 | 8/1990 | Ott | 564/406 |
| 5,262,539 | 11/1993 | Makosza et al. | 546/307 |
| 5,466,781 | 11/1995 | Seko | 564/395 |

FOREIGN PATENT DOCUMENTS 3612238  10/1987  Germany.

OTHER PUBLICATIONS

O. Westphal, "Uber die Alkylierung des Hydrazins," *Ber.* vol. 74 (1941), p. 759.
E. Y. Spencer, et al., "Preparation of Pyramide," *Can. J. Res.*, vol. 24B (1946) pp. 204–207.
J. R. Holden, et al., "Head Resistant Explovies VI: Properties of 1,3–Diamino–2,4,6–Trinitrobenzene, DATB," *NAVORD Report 6299* (Mar. 17, 1959).
G. M. Omietanski, et al., "The Reaction of Chloramine with Tertiary Amines. 1,1,1–Trisubstituted Hydrazinium Salts," *J.ACS.*, vol. 78 (1956) pp. 1211–1213.
S. K. Yasuda, "Identification of 1,3,5–Triamino–2,4,6–Trinitrobenzene Impurities by Two–Dimensional Thin–Layer Chromatography," *Journal of Chromatography*, vol. 71 (1972), pp. 481–486.
T. Urbanski and S. K. Vasudeva, "Heat Resistant Explosives," *Journal of Scientific Industrial Research*, vol. 37 (May 1978), pp. 221–280.
W. P. Norris and A. P. Chatin, "CL–14, A New Dense, Insensitive, High Explosive (u)," *NWC TP 6597* (May 1985).
R. L. Atkins, et al., "Synthesis of Polynitro Compounds. Hexasubstituted Benzenes," *J. Org. Chem.*, vol. 51 (1986), pp. 3261–3266.
M. Makosza, et al., "Vicarious Nucleophilic Substitution of Hydrogen," *Acc. Chem. Res.*, vol. 20 (1987), pp. 282–289.
W. Worthy, "Shock Sensitivity of Explosives Clarified," *C&EN*, Aug. 10, 1987, p. 25.
M. Makosza, "Amination of Nitroarenes with Sulfenamides via Vicarious Nucleophilic Substitution of Hydrogen," *J. Org. Chem.* vol. 57 (1992), pp. 4784–4885.
A. R. Mitchell, et al., "Advances in the Chemical Conversion of Energetic Materials to Higher Value Products," Presentation at Life Cycles of Energetic Materials, Del Mar, CA, Dec. 11–16, 1994.
J. G. Keay, et al., "Regiospecific synthesis of 1–substituted–1,2,4–triazoles using 4–amino–1,2,4–triazole".
Katrizky et al., J. Org. Chem. 1986, vol. 51, 5039–5040.
Katrizky et al., J. Org. Chem. 1988, vol. 53, 3978–3982.
Mitchell et al., 24th Intl. Annual. Conference of ICT, Karlsruhe, Germany, pp. 38–1–38–6. 1993.

*Primary Examiner*—Charles T. Jordan
*Assistant Examiner*—John R. Hardee
*Attorney, Agent, or Firm*—Henry P. Sartorio

[57] ABSTRACT

The present invention relates to a process to produce 1,3-diamino-2,4,6-trinitrobenzene (DATB) or 1,3,5-triamino-2,4,6,-trinitrobenzene (TATB) by:

(a) reacting at ambient pressure and a temperature of between about 0° and 50° C. for between about 0.1 and 24 hr, a trinitroaromatic compound of structure V:

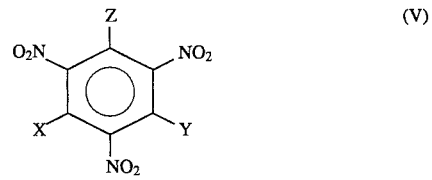

(V)

wherein X, Y, and Z are each independently selected from —H, or —NH$_2$, with the proviso that at least 1 or 2 of X, Y, and Z are hydrogen, with an amount effective to produce DATB or TATB of 1,1,1-trialkylhydrazinium halide wherein alkyl is selected from methyl, ethyl, propyl or butyl and halide is selected from chloride, bromide or iodide.

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformide, dimethylacetamide and mixtures thereof, provided that when alcohols are present primarily DATB and picramide is formed; and (b) isolating the DATB or TATB produced. DATB and TATB are useful specialty explosives. TATB is also used for the preparation of benzenehexamine, a starting material for the synthesis of novel materials (optical imaging devices, liquid crystals, ferromagnetic compounds).

20 Claims, No Drawings

VICARIOUS NUCLEOPHILIC SUBSTITUTION TO PREPARE 1,3-DIAMINO-2,4,6-TRINITROBENZENE OR 1,3,5-TRIAMINO-2,4,6-TRINITROBENZENE

ORIGIN OF THE INVENTION

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

1. Field of the Invention

The present invention concerns the discovery and use of 1,1,1-trisubstituted hydrazinium salts in vicarious nucleophilic substitution (VNS) reactions, which provide new and improved syntheses of DATB and TATB.

2. Description of the Problem and Related Art

Some explosives are more sensitive to shock and heat than others having a similar structure. Studies of explosives based on the benzene ring include, for example, 1,3,5-trinitrobenzene (TNB), 2,4,6-trinitrotoluene (TNT), 1-monoamino-2,4,6-trinitrobenzene (MATB) (aka picramide), 1-3-diamino-2,4,6-trinitrobenzene (DATB) and 1,3,5-triamino-2,4,6-trinitrobenzene (TATB). Although these compounds have much in common, the shock initiation thresholds, that is, the shock pressure required to cause detonation in 50% of the tests, vary widely. Table 1 shows the pattern.

TABLE 1

| SHOCK INITIATION THRESHOLD OF EXPLOSIVES | |
|---|---|
| Compound | Pressure (kilobars) |
| TNB | 17 |
| TNT | 21 |
| MATB | 30 |
| DATB | 46 |
| TATB | 75 |

While not wanting to be bound by theory, it appears that adding amino groups to a nitro-substituted benzene ring raises the initiation shock threshold. This pattern occurs, because as the networks of hydrogen bonds increase, the networks absorb energy from a shock front and reduce the amount of shock that goes to the ring itself. See W. Worthy in "Shock Sensitivity of Explosives Clarified", *Chemical and Engineering News*, p. 25, (Aug. 10, 1987) for further discussion.

It follows that DATB and TATB are highly desirable, insensitive explosives that are used primarily in specialty applications. Part of the reason that they are used in special as opposed to general explosive applications is high cost. They are too expensive to use in ordinary applications when other less expensive explosives can be used. One reason that TATB is expensive is that it is usually prepared from 1,3,5-trichlorobenzene which is expensive and is not generally available from domestic suppliers. The chloride byproduct ($NH_4Cl$) is difficult to remove completely and may cause compatibility problems in certain types of ordnance (cf. U.S. Pat. No. 4,032,377).

Alternative preparations were sought, and

T. M. Benziger, U.S. Pat. No. 4,032,377 discloses a preparation of TATB by nitration of 1,3,5-trichlorobenzene to 1,3,5-trichloro-2,4,6-trinitrobenzene followed by treatment with ammonia to produce TATB. This patent also discloses the use of water to separate the byproduct ammonium chloride.

D. G. Ott and T. M. Benziger, U.S. Pat. No. 4,952,733 and *Journal Of Energetic Materials*, vol. 5, pp. 343–354 (1987) disclose a preparation of TATB by nitration of 3,5-dichloroanisole to produce 3,5-dichloro-2,4,6-trinitroanisole which is chlorinated to give 1,3,5-trichloro-2,4,6-trinitrobenzene which is ammonolyzed to give TATB.

Additional art of interest includes, for example:

R. T. Atkins et al., in U.S. Pat. No. 4,248,798 disclose a new method for preparing pentanitroaniline (PNA) and triaminotrinitrobenzene (TATB) from TNT. TNT is first reduced using $H_2S$ to 4-amino-2,6-dinitrotoluene then nitrated using nitric acid/sulfuric acid to pentanitroaniline followed by reaction with ammonia to produce the TATB.

M. Makosza et al., review and discuss "Vicarious Nucleophilic Substitution of Hydrogen", in *Accounts of Chemical Research*, vol. 20, pp. 282–9 (1987), and teach the substitution of polynitrobenzene structures with a number of non-nitrogen containing vicarious nucleophilic substitution reagents. No nitrogen-containing reagents are suggested.

A. R. Katritzky and K. S. Laurenzo, *Journal of Organic Chemistry*, vol. 51, pp. 5039–5040 (1986) disclose monoamination of nitrobenzene and some substituted nitrobenzenes to give 4-nitroanilines by VNS reactions. The same authors, in the *Journal of Organic Chemistry*, vol. 53, pp. 3978–3982 (1988) disclose the use of a series of 4-(alkylamino)-1,2,4-triazoles to transfer the alkylamino group to the 4-position of nitrobenzene and 3-substituted nitrobenzenes by VNS.

T. Urbanski et al., *Journal of Scientific and Industrial Research* (India), vol. 37, p. 250–5 (1978), disclose the standard preparation and properties of several heat resistant explosives including DATB and TATB.

J. R. Holden et al., U.S. Naval Ordnance Laboratory, White Oak, Md., NAVORD Report 6299 (March 1959), disclose the properties of DATB.

S. K. Yasuda et al., in *Journal of Chromatography*, vol. 71, p. 484–86 (1972) discuss the separation and identification of 12 impurities of 1,3,5-triamino-2,4,6-trinitrotoluene by two dimensional thin-layer chromatography.

M. Makosza et al., *Journal of Organic Chemistry*, vol. 57, p. 4784–5 (1992), disclose the mono-amination of nitrobenzenes with sulfenamides via vicarious nucleophilic substitution of hydrogen.

W. P. Norris et al., "CL-14, A New Dense, Insensitive, High Explosive", Naval Weapons Center, China Lake, Calif., Report No. TP 6597 (Unclassified), May 1985, disclose the use of hydroxylamine to di-aminate 4,6-dinitrobenzofuroxan (DNBF) thereby producing 5,7-diamino-4,6-dinitrobenzofuroxan (CL-14).

R. T. Atkins et al., in the *Journal of Organic Chemistry*, vol. 51, pp. 3261–3266 (1986), disclose the synthesis of a number of polynitro compounds, including TATB. Pentanitroaniline is reacted with ammonia to produce TATB.

T. R. Gibbs et al., *LASL Explosives Properties Data* (University of California Press, Berkeley, Calif., 1980.

B. M. Dobratz, *LLNL Explosives Handbook: Properties Of Chemical Explosives and Explosive Simulants*, Lawrence Livermore National Laboratory, Livermore, Calif., UCRL-52997 (March 16, 1981 ).

German patent, Ger. Offen DE 3,612,238) teaches the use of TATB to prepare components of lyotropic liquid-crystal phases for use in display devices.

None of these references individually or collectively teach or suggest the present invention.

It is apparent from this description that there is a need for a new process that is milder and more environmentally benign to easily convert nitroaromatic compounds to DATB, TATB or mixtures thereof. The present invention provides such useful processes which avoid strong acids ($H_2SO_4$, $HNO_3$) at elevated temperatures (100°–150° C.) and the need for noxious materials such as ammonia, thionyl chloride and hydrogen sulfide. These processes are also environmentally benign.

SUMMARY OF THE INVENTION

The present invention relates to a process to produce 1,3-diamino-2,4,6-trinitrobenzene (DATB) or 1,3,5-triamino-2,4,6,-trinitrobenzene (TATB) by:

(a) reacting at ambient pressure and a temperature of between about 0° and 50° C. for between about 0.1 and 24 hr, a trinitroaromatic starting material compound V:

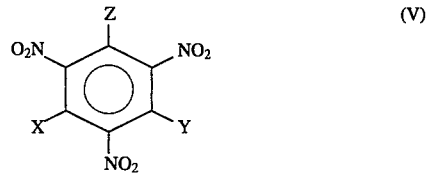

wherein X, Y, and Z are each independently selected from the group consisting of —H, —$CH_3$, and —$NH_2$, with the proviso that at least 1 or 2 of X, Y, and Z are hydrogen, with an amount effective to produce DATB or TATB of 1,1,1,-trialkyl hydrazinium halide wherein alkyl is selected from methyl, ethyl, propyl or, butyl or benzyl and halide is selected from chloride, bromide or iodide.

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed; and (b) isolating the DATB or TATB produced.

Preferably, X, Y and Z are each independently selected from —H or $NH_2$.

In another aspect, the present invention concerns a process to produce 1,3-diamino- 2,4,6-trinitrobenzene (DATB) or 1,3,5-triamino-2,4,6,-trinitrobenzene (TATB):

(a) by obtaining an aromatic compound of the structure:

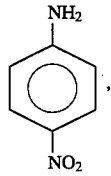

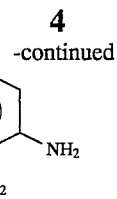

mixtures thereof from commercial sources or by:

(i) reacting

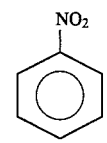

at a temperature of between about 0° and 50° C. for between about 0.1 and 24 hr with an effective amount of 1,1,1,-trialkylhydrazinium halide wherein alkyl is selected from methyl, ethyl, propyl, butyl, or benzyl and halide is selected from chloride, bromide or iodide to produce compound III or compound IV;

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of dimethylformamide, dimethylacetamide, or mixtures thereof, and isolating the product which is III and/or compound VI;

(ii) or nitrating aniline using a mixture of nitric acid and sulfuric acid to produce compound III and IV; or (iii) nitrating acetanilide using a mixture of nitric acid and sulfuric acid to produce 4-nitroacetanilide and nitrating further using a mixture of nitric acid and sulfuric acid to produce compound VI;

(b) reacting 2-nitroaniline, 4-nitroaniline or combinations thereof with a nitric acid, and sulfuric acid mixture under conditions to produce 2,4,6-trinitroaniline (VI);

(c) reacting at ambient pressure and a temperature of between about 0° and 50° C. for between about 0.1 and 24 hr a trinitroaromatic compound V or VI:

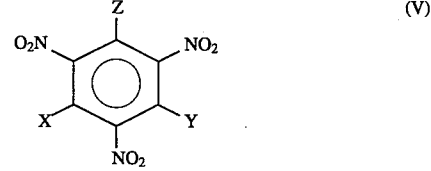

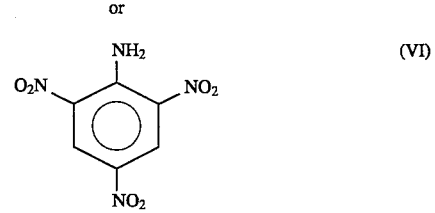

wherein X, Y, and Z are each independently selected from the group consisting of —H, —$CH_3$ and —$NH_2$, with the proviso that at least 1 or 2 of X, Y, and Z is hydrogen;

with an effective amount of 1,1,1-trialkylhydrazinium halide wherein alkyl is selected from methyl, ethyl, propyl butyl or benzyl and halide is selected from chloride, bromide or iodide;

in the presence of a base selected from the group consisting or sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (B) isolating the DATB or TATB produced.

Preferably, DATB is produced when the 1,1,1-trialkylhydrazinium halide is present in between about 1.9 and 2.3 molar equivalents per mole of compound V.

Preferably, structure V is selected from 1,3,5-trinitrobenzene, 2,4,6-trinitroaniline, 1,3-diamino-2,4,6-trinitrobenzene, 2,4,6-trinitrotoluene.

Preferably, the 1,1,1 -trialkylhydrazinium halide is 1,1,1 -trimethylhydrazinium iodide.

Preferably, the strong base is selected from sodium methoxide or potassium tert-butoxide.

Preferably, the solvents are selected from the group consisting of methanol, ethanol, propanol, butanol, dimethylsulphoxide, N-methylpyrrolidone, hexamethylphosphoramide, dimethylformamide, dimethylacetamide and mixtures thereof provided that when alcohols are present primarily DATB and picramide are formed.

Preferably, TATB is produced when the 1,1,1-trialkylhydrazinium halide is present in between about 3.9 and 5.5 molar equivalents per mole of compound V.

In another aspect, the present invention includes:

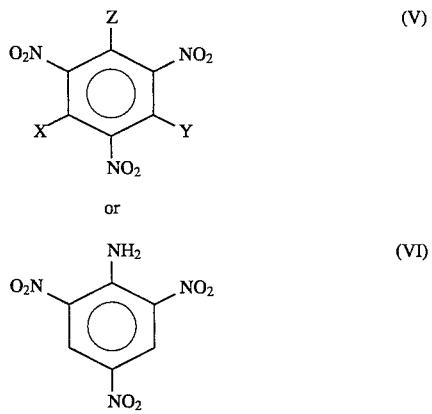

wherein X, Y, and Z are each independently selected from the group consisting of —H, —CH$_3$, and —NH$_2$, with the proviso that at least 1 or 2 of X, Y, and Z is hydrogen, with an effective amount of 1,1,1-trialkylhydrazinium halide wherein alkyl is selected from methyl, ethyl, propyl or butyl and halide is selected from chloride, bromide or iodide, in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (B) isolating the DATB or TATB produced.

In another embodiment of the process, the reaction temperature is between about 10° and 30° C.

In another aspect, the present invention concerns a process to produce mono or polyamino, mono or poly nitrobenzene, which process comprises:

(A) obtaining an aromatic compound selected from the following:

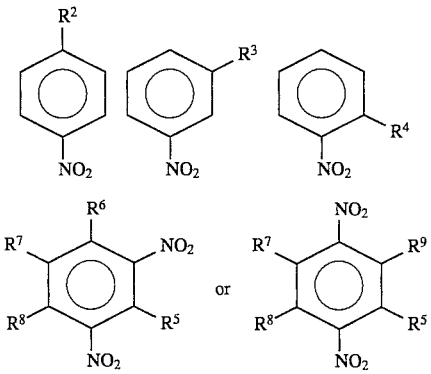

wherein R$^2$, R$^3$, and R$^4$ are each independently selected from —H, —CH$_3$, F, —Cl, —Br, —I, CN or OCH$_3$, and R$^5$-R$^9$ are each independently selected from —H, —CH$_3$, F, —Cl, —Br, —I, —CN or —OCH$_3$ or mixtures, with the proviso that at least one or R$^5$-R$^9$ is H;

(B) reacting at ambient pressure and a temperature of between about 0° and 50° C. for between about 0.1 and 24 hr a nitro aromatic compound;

with an effective amount of 1,1,1,-dialkyl-1,2-di-R-(where R=hydrogen alkyl or aryl) hydrazinium halide wherein alkyl is selected from methyl, ethyl, propyl or butyl, R is selected from H, C$_1$-C$_{20}$ alkyl, or aryl, and halide is selected from chloride, bromide or iodide, in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (B) isolating the monoamino, diamino or triaminosubstituted nitroaromatic compound produced.

DETAILED DESCRIPTION OF THE INVENTION AND PREFERRED EMBODIMENTS

Definitions

As used herein:

"DMF" refers to dimethylformamide.

"DMAC" refers to dimethylacetamide.

"DATB" refers to 1,3-diamino-2,4,6-trinitrobenzene.

"DMSO" refers to dimethylsulphoxide.

"HMPA" refers to hexamethylphosphoramide.

"NB" refers to nitrobenzene.

"NMP" refers to N-methypyrrolidone.

"NT" refers to nitrotoluene.

"Picramide" or "TNA" refers to 1-amino-2,4,6-trinitrobenzene.

"TATB" refers to 1,3,5-triamino-2,4,6-trinitrobenzene.

"TAHI" refers to trialkylhydrazium iodide.

"TMHI" refers to triamethylhydrazinium iodide.

"TNB" refers to 1,3,5-trinitrobenzene.

"TNT" refers to 2,4,6-trinitrotoluene.

The present invention includes the preparation of DATB and TATB. TATB is also useful in the preparation of liquid crystals.

In the present invention, the starting material, a mononitrated, dinitrated or trinitrated benzene structure is contacted with strong base in the presence of a solvent at between about 0° and 50° C. and ambient pressure for between about 0.1 and 24 hr, preferably between about 1 and 5 hr. Preferably, the temperature is between about 10° and 30° C., and more preferably about ambient temperature (i.e. 20° C.).

The nitrated aromatic compound is reacted with 1,1,1-trialkylhydrazinium halide to provide amino-substituted aromatic compounds by VNS.

*Chemical and Engineering News*, May 8, 1995, p. 21 discloses that the, Defense Nuclear Agency has given a contract to Thiokol Corp. to dispose of liquid propellant dimethyl hydrazine (the starting material for trimethylhydrazinium halide from Russian intercontinental ballistic missiles by converting the fuel into commercial commodity chemicals. These chemicals can be sold to companies making rubber, fungicides, solvents, plastics, and other products. Also see H. H. Szmant, *Organic Building Blocks of the Chemical Industry*, John Wiley and Sons, New York, 1989, p. 83.

G. M. Omietanski et al., *Journal of the American Chemical Society*, vol. 78, p. 1211–1213 (1956), disclose the preparation of alkyl and cycloalkyl hydrazinium chlorides. O. Westphal, in *Chem. Ber.*, vol. 74, 759ff (1941), disclose a preparation of quaternized hydrazines.

The extent of the amination using the 1,1,1-trialkylhydrazinium halide is normally controlled by judicious choice of temperature, time, solvents, strong base and amount of 1,1,1-trialkylhydrazinium halide. Alcohol solvents usually limit the: reaction to production of DATB and picramide because alcohols appear to slow or stop complete amination. The amount of reagent is also important to produce DATB, i.e. between about 1.9 and 2.3 molar equivalents per mole of structure V, preferably about 2.1 eq.

Solvents—In the present invention, solvents which are preferred include aliphatic alcohols having 1–6 carbon atoms (all isomers), cycloalkyl alcohols having 1–6 carbon atoms and the like. Useful dipolar aprotic solvents include, dimethylsulphoxide N-methylpyrrolidone, hexamethylphosphoramide, dimethylformamide, diethylformamide, dimethylacetamide and the like. The solvent may also include diluents (benzene, chloroform) as needed to optimize conditions and product yields. Mixtures of solvents are also included.

Strong Bases—In the present invention, strong bases are usually the alkali metal salts of alcohols. Alcohols having 1–15 carbon atoms are preferred, more preferred are alcohols having 1–10 carbon atoms, and most preferably are alcohols having 1–6 carbon atoms. Especially preferred alcohols include methanol, ethanol, propanol, (n- or iso-) and butanol (n-, iso-, sec-, or tert-).

This methodology is extended to the introduction of alkyl- or aryl-substituted amines to electrophilic aromatic rings. This may be accomplished by reaction of the electrophilic aromatic ring with a 1,1-dialkyl-1,2-di-R (R=alkyl or aryl) hydrazinium halide in DMSO in the presence of base. In 1,1 -dialkyl-1,2-di-R-hydrazinium halide, R is aryl selected from phenyl, benzyl, ethylenephenyl, naphthyl, pyridine, pyrimidine, quinoline, quinoxaline, imidazole, triazole, triazine, pyrazole and the like.

The 1,1-dialkyl-1,2-di-R (R=alkyl or aryl) hydrazinium halide is synthesized by two general methods:

1. The reaction of a symmetrical hydrazine bearing an alkyl or aryl radical with methyl iodide produces a 1,1-dimethyl-1,2-dialkyl (or aryl) hydrazinium iodide. The identity of the substituted amine which is transferred in the VNS reaction is determined by the selection of the R- group on the symmetrical hydrazine starting material. Therefore:

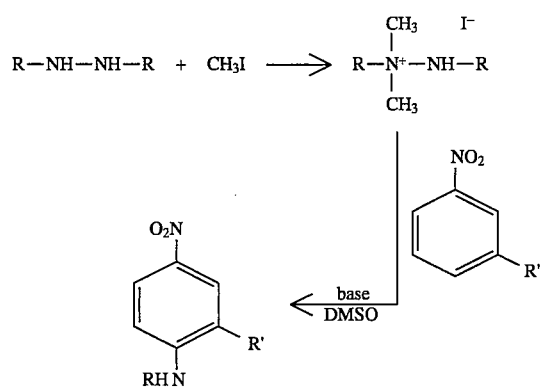

(see O. Westphal, *Chem. Ber.*, (1941), 1362).

2. The reaction of a trialklylhydrazinium halide with an alkyl or acyl halide in the presence of base yields a 1,1,1-trialkyl-2-(R)-hydrazinium halide or the corresponding ylide. Therefore:

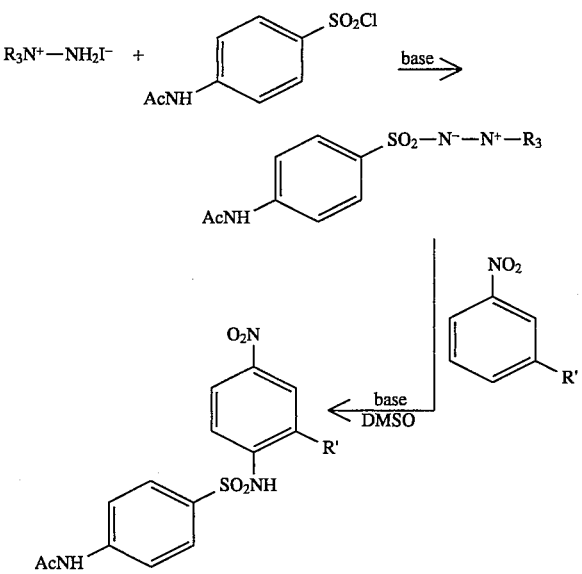

(see J. N. Ashley, et al., *J. Chemical Soc.*, (1947), p. 60).

The VNS reaction is applied to substituted aromatics bearing at least one nitro-group. The aromatic group include heterocycles such as substituted and unsubstituted pyridine, pyrimidine, pyrazine, quinoline, quinoxalines, imidazole, triazole and pyrazoles.

The use of 1,1,1 -triakylhydrazinium halides and 1,1 -dialkyl-1,2-di-R (R= alkyl or aryl) hydrazinium halides as VNS reagents to add amino-groups to electrophilic aromatic rings have not yet been described. The general utility of these reagents to add amino groups to nitro-substituted aryls is also claimed.

3. This methodology is extended to synthesis of polymeric VNS reagents for the introduction of amino groups onto electrophilic aromatic rings. Thus, chloromethyl-substituted polystyrene is reacted with VDMH (1,1-dimethylhydrazine to yield a polymeric 1,1,1-trialkylhydrazinium chloride which is used in unsymmetrical VNS reactions to introduce amino-groups onto electrophilic aromatic rings.

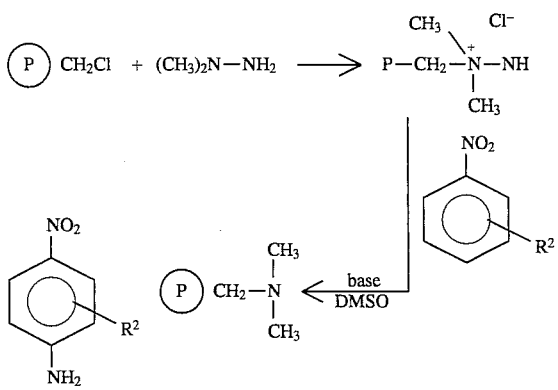

The spent polymeric VNS reagent is then regenerated by reaction with chloramine.

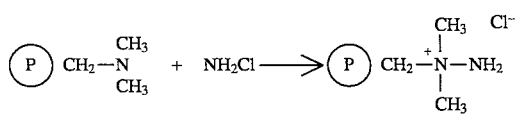

(see G. M. Omietanski, et al., *J. Chemical Society*, (1956), p. 1211–13).

The following Examples are presented to be descriptive and illustrative only. They are not to be construed to be limiting in any way.

General

Picramide is obtained from commercial sources or prepared according to E. Y. Spencer et al., *Canadian Journal Research*, vol. 24B, pp. 204–207 (1946).

1,3,5-Trinitrobenzene is obtained from commercial sources or prepared according to *Organic Synthesis*.

2,4,6-Trinitrotoluene is obtained from commercial sources or is prepared according to any literature source.

DMSO is dried and stored over 4A molecular sieves.

Anhydrous calcium sulfate is used to protect VNS reactions from atmospheric moisture.

EXAMPLE 1

Preparation of Quaternary Hydrazinium Salts
1,1,1-Trimethylhydrazinium Iodide (TMHI)

(a) 1,1-Dimethylhydrazine (5.1 ml, 67 mmol) is dissolved in 60 ml of tetrahydrofuran (THF). Methyl iodide (4 ml, 67 mmol) is added with ice-bath cooling and mechanical stirring. The resulting slurry is diluted with THF to facilitate stirring. The reaction mixture is stirred at ambient temperature for 2 hr, and a while solid is collected by filtration. Recrystallisation from ethanol (100 ml) yields 11.6 G of TMHI (86%) as white plates; m.p. 230°–232° C. (softening at 223° C.); $^1$H-nmr (D$_2$O) $\delta$ 3.42 (—CH$_3$) 4.55 ppm (NH$_2$ exchangeable).

(b) Similarly, Example 1(a) is repeated except that 1,1-dimethylhydrazine is replaced by a stoichiometrically equivalent amount of 1,2-di-R (where R=alkyl or aryl) hydrazine and a similar amount of 1,1,-dimethyl-1,2-di-R-hydrazinium iodide iodide is produced.

(c) Similarly, when Example 1(a) is repeated except that methiodide is replaced by a stoichiometrically equivalent amount of ethyl chloride and reacted with 1,1-diethylhydrazine to produce a similar amount of 1,1,1-triethylhydrazinium chloride.

EXAMPLE 2

Preparation of DATB from Picramide (a) Picramide (0.30 g, 1.3 mmol) and TMHI (0.56 g, 2.8 mmol) are dissolved in 10 ml of dry dimethylsulphoxide (DMSO) with protection from atmospheric moisture. Sodium methoxide (0.31 g, 5.7 mmol) is added in one portion with stirring and the resulting red slurry is stirred at ambient temperature for 3 hr. The reaction mixture is poured into ice water (25 ml) and acidified to pH 4 with hydrochloric acid. The= product is collected by filtration, washed with water and dried to yield 0.24 g (75%) of beige-yellow solid. The IR spectra for this material and a reference sample of DATB are identical.

(b) Similarly, Example 2(a) is repeated except that 1,1,1-trimethylhydrazinium iodide is replaced by a stoichiometrically equivalent amount of 1,1,1-triethylhydrazinium chloride, and a similar amount of DATB is produced.

(c) Similarly, when Example 2(a) is repeated except that DMSO is replaced by a volumetrically equivalent amount of methanol, ethanol n-propanol, iso-propanol or normal butanol, and the base is sodium methoxide, sodium ethoxide, sodium n-propoxide, sodium isopropoxide, or potassium tert-butoxide, a mixture of picramide and DATB is produced. The DATB is purified by crystallization from DMF or DMSO.

EXAMPLE 3

Preparation of TATB from Picramide (a) Picramide (1.00 g, 4.38 mmol) and TMHI (3.54 g, 17.5 mmol) are dissolved in dry DMSO (34 ml). Sodium methoxide (1.89 g, 35.0 mmol) is added in one portion and the resulting red slurry is stirred for 16 hr at ambient temperature under a dry atmosphere. The reaction mixture is poured into ice water and acidified to pH 4 with concentrated hydrochloric acid. The resulting precipitate is collected, and washed with water (20 ml) and acetone (10 ml) to yield 1.07 g (95%) of beige-yellow powder; m.p. 355° C. with decomposition. The IR spectra for this material and TATB are identical.

(b) Similarly, Example 3(a) is repeated except that 1,1,1-trimethylhydrazinium iodide is replaced by a stoichiometrically equivalent amount of 1,1,1-triethylhydrazinium chloride, and a similar amount of TATB is produced.

(c) Similarly, when Example 3(a) is repeated except that DMSO is replaced by a volumetrically equivalent amount of DMF, or DMAC, and sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 4

Preparation of DATB from TNB (a) DMSO (5 ml) is added with rapid stirring to a mixture of TNB (0.148 g, 0.695 mmol), TMHI (1.03 g, 5.10 mmol) and sodium methoxide (0.609 g, 11.3 mmol). The dark brown suspension is stirred at ambient temperature for 2 hr. The reaction mixture is poured into cold 0.12N aqueous HCl (200 ml). The resulting precipitate is collected, washed with water and dried to give 0.148 g (61%) of a dark orange solid. The IR spectra for this material and DATB are identical.

(b) Similarly, Example 4(a) is repeated except that 1,1,1-trimethylhydrazinium iodide is replaced by a stoichiometrically equivalent amount of 1,1,1-triethylhydrazinium chloride, and a similar amount of DATB is produced.

(c) Similarly, when Example 4(a) is repeated except that DMSO is replaced by a volumetrically equivalent amount of DMF or DMAC and sodium methoxide is replaced by a stoichiometrically equivalent amount of sodium ethoxide, sodium n-propoxide, sodium isopropoxide, or sodium tert-butoxide respectively, a mixture of picramide and DATB is produced. The DATB is purified by crystallization from DMF and DMSO.

EXAMPLE 5

Preparation of TATB from TNB (a) TNB (0.148 g, 0.693 mmol) and TMHI (1.03 g, 5.10 mmol) are dissolved in DMSO (10 ml) prior to the addition of sodium methoxide (0.600 g, 11.1 mmol). The dark brown suspension is stirred for 20 hr at ambient temperature. The reaction mixture is poured into cold 0.12N aqueous HCl (200 ml). The resulting precipitate is washed with water and dried to give 0.158 g (61%) of a light brown powder having the IR spectrum of TATB.

(b) Similarly, Example 5(a) is repeated except that 1,1,1-trimethylhydrazinium iodide is replaced by a stoichiometrically equivalent amount of 1,1,1-triethylhydrazinium chloride, and a similar amount of TATB is produced.

(c) Similarly, when Example 5(a) is repeated except that DMSO is replaced by a volumetrically equivalent amount of DMF, DMAC, and sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 6

Preparation of Nitroanilines from Nitrobenzene (a) Nitrobenzene (0.133 ml, 1.29 mmol) and TMHI (0.283 g, 1.40 mmol) are dissolved in 7 ml DMSO. Potassium tert-butoxide (0.348 g, 3.10 mmol) is added in one portion and the resulting dark red-orange solution is stirred for 4 hr at ambient temperature. The reaction mixture is poured over 5 g ice, acidified with 10% hydrochloric acid and stirred for 0.5 hr. The resulting solution is extracted with ethyl acetate (3×20 ml). The combined organic layers are washed with water, dried (MgSO$_4$) and evaporated. The resulting brown solid is chromatographed using silica gel eluted with, 9:1 petroleum ether-acetone to yield 0.096 g o-nitroaniline and 0.062 g p-nitroaniline (0.158 g total, 86% overall yield) in the relative isomer ratio of 61:39.

(b) Similarly, Example 6(a) is repeated except that 1,1,1-trimethylhydrazinium iodide is replaced by a stoichiometrically equivalent amount of 1,1,1-triethylhydrazinium chloride, and a similar amount of nitroanilines are produced.

(c) Similarly, when Example 6(a) is repeated except that DMSO is replaced by a volumetrically equivalent amount of DMF or DMAC, and potassium tert-butoxide is replaced by a stoichiometrically equivalent amount of sodium methoxide, sodium ethoxide, sodium n-propoxide, sodium isopropoxide, or sodium tert-butoxide respectively, a similar amount of nitroanilines are produced.

EXAMPLE 7

Amination of 3-Substituted Nitrobenzenes with TMHI

TMHI is reacted with the same 3-substituted nitrobenzene substrates used with 4-amino-1,2,4-triazole (ATA) as reported by A. R. Katritzky and K. S. Laurenzo, *Journal of Organic Chemistry*, vol. 51, pp. 5039–5040 (1986). The nitroaromatic substrate (1.3 mmol) and TMHI (1.4–1.9 mmol) are dissolved in dry DMSO (7 ml), -and solid alkoxide (sodium methoxide or potassium tert-butoxide) is added with stirring. The solution immediately becomes nearly black in color. After 4–17 hr of stirring at room temperature, the reaction is quenched with 10% HCl. Precipitated solids are collected by filtration and washed with cold water. The filtrate is extracted with ethyl acetate and the crude products obtained upon evaporation of the solvent are subjected to chromatography on silica. The identity of all products is confirmed by comparison of melting points and/or $^1$H NMR with authentic standards. The results are summarized in Table I.

Table I shows that TMHI is not as selective as ATA, producing in most cases multiple regioisomeric products. TMHI displays a tendency to aminate in the 2-position which contrasts with exclusive 4-amination in the case of ATA. The very high reactivity of TMHI is of interest and with m-dinitrobenzene-2,4-diamination takes place even under substoichiometric conditions.

TABLE 1

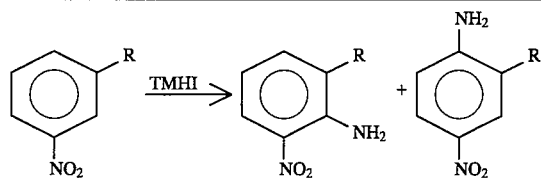

| AMINATION OF 3-SUBSTITUTED NITROBENZENES | | | |
|---|---|---|---|
| R | Total Yield (%) | position of NH$_2$a | % isomer |
| H | 85 | 2 | 61 |
|   |    | 4 | 39 |
| CH$_3$ | 84 | 2 | 38 |
|   |    | 4 | 35 |
|   |    | 6 | 27 |
| Cl | 82 | 2 | 32 |
|   |    | 4 | 49 |
|   |    | 6 | 19 |
| OCH$_3$ | 66 | 2 | 90 |
|   |    | 4 | 10 |
| F | 84 | 2 | 45 |
|   |    | 4 | 47 |
|   |    | 6 | 8 |
| I | 76 | 2 | 45 |
|   |    | 4 | 37 |
|   |    | 6 | 17 |
| CN | 41 | 2 | 20 |
|   |    | 4 | 44 |
|   |    | 6 | 36 | aRelative to NO$_2$

EXAMPLE 8

Preparation of Diamino-TNT (DATNT) from TNT (a) TNT (0.227 g, 1.00 mmol) and TMHI (1.03 g, 5.10 mmol) are dissolved in DMSO (10 ml). Sodium methoxide (0.600 g, 11.1 mmol) is added in one portion with stirring. The dark brown suspension is stirred for 23 hr at ambient temperature. The reaction mixture is poured into cold 0.12N aqueous HCl (200 ml) and stirred for 20 minutes prior to the collection of precipitate. The product is washed with water and dried to give 0.212 g (82%) of DATNT as a dark, olive green solid; $^1$H-nmr (DMSO-d$_6$) δ 8.08 (br s, 4, NH$_2$) and 2.18 (s,3,ArCH$_3$).

(b) Similarly, Example 8(a) is repeated except that 1,1,1-trimethylhydrazinium iodide is replaced by a stoichiometrically equivalent amount of 1,1,1-triethylhydrazinium chloride, and a similar amount of DATNT is produced.

(c) Similarly, when Example 5(a) is repeated except that DMSO is replaced by a volumetrically equivalent amount of DMF or DMAC, and sodium methoxide is replaced by a stoichiometrically equivalent amount of sodium ethoxide, sodium n-propoxide, sodium isopropoxide, or potassium tert-butoxide respectively, a similar amount of DATNT is produced.

While only a few embodiments of the present invention have been shown and described herein, it is apparent to those skilled in the art that various modifications and changes can be made in these novel processes using 1,1,1-trialkyl hydrazinium halide to produce DATB or TATB without departing from the spirit and scope of the present invention. All such modifications and changes coming within the scope of the appended claims are intended to be covered thereby. In this application primarily means that DATB or TATB is produced in about 70% yield or greater, preferably about 80% yield or greater, and more preferably about 90% yield or greater.

We claim:

1. A process to produce 1,3-diamino-2,4,6-trinitrobenzene (DATB) or 1,3,5-triamino-2,4,6,-trinitrobenzene (TATB), which process comprises:

(a) reacting at ambient pressure and a temperature of between about 0° and 50° C. for between about 0.1 and 24 hr, a trinitroaromatic starting material compound V:

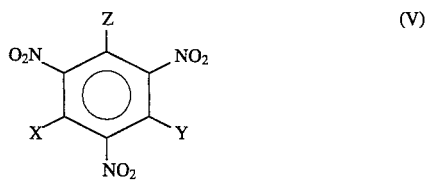

(V)

wherein X, Y, and Z are each independently selected from the group consisting of —H, —CH$_3$, and —NH$_2$, with the proviso that at least 1 of X, Y, and Z is hydrogen, with an amount of 1,1,1-trialkylhydrazinium halide effective to produce DATB or TATB, wherein alkyl is selected from methyl, ethyl, propyl, butyl or benzyl and halide is selected from chloride, bromide or iodide.

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof; provided that when alcohols are present primarily DATB and picramide are formed; and (b) isolating the DATB or TATB produced.

2. The process of claim 1 wherein the reaction temperature is between about 10° and 30° C. and X, Y and Z are each independently selected from —H or —NH$_2$.

3. The process of claim 2 wherein DATB is produced and the 1,1,1-trialkylhydrazinium halide is present in between about 1.9 and 2.3 molar equivalents per mole of starting material compound V.

4. The process of claim 2 wherein starting material compound V is selected from 1,3,5trinitrobenzene, 2,4,6-trinitroaniline, or 1,3-diamino-2,4,6-trinitrobenzene.

5. The process of claim 2 wherein the 1,1,1-trialkylhydrazinium halide is 1,1,1-trimethylhydrazinium iodide.

6. The process of claim 2 wherein the strong base is selected from sodium methoxide or potassium tert-butoxide.

7. The process of claim 2 wherein the solvents are methanol, ethanol, propanol, butanol or a mixture thereof.

8. The process of claim 3 wherein starting material compind V is selected from 1,3,5-trinitrobenzene, 2,4,6-trinitroaniline;

the 1,1,1-trialkylhydrazinium halide is 1,1,1-trimethylhydrazinium iodide;

the strong base is selected from sodium methoxide or potassium tert-butoxide; and the solvent is selected from methanol, ethanol, propanol, butanol, dimethylsulphoxide, N-methylpyrrolidone, hexamethylphosphoramide, dimethylformamide, dimethylacetamide or mixtures thereof.

9. The process of claim 2 wherein TATB is produced and the 1,1,1trialkylhydrazinium halide is present in between about 3.9 and 5.5 molar equivalents per mole of compound V.

10. The process of claim 9, wherein structure the starting material compound is selected from 1,3,5trinitrobenzene, 2,4,6-trinitroaniline, or 1,3-diamino-2,4,6'-trinitrobenzene.

11. The process of claim 9 wherein the 1,1,1-trialkylhydrazinium halide is 1,1,1-trimethylhydrazinium iodide.

12. The process of claim 9 wherein the strong base is selected from sodium methoxide or potassium tert-butoxide.

13. The process of claim 9 wherein the solvent is a dipolar aprotic solvent selected from dimethylsulphoxide, N-methylpyrrolidone, hexamethylphosphoramide, dimethylformamide, dimethylacetamide, or mixtures thereof.

14. The process of claim 9 wherein the starting material compound is selected from 1,3,5-trinitrobenzene, 2,4,6-trinitroaniline, or 1,3-diamino-2, 4,6-trinitrobenzene;

the 1,1,1-trialkylhydrazinium halide is 1,1,1-trimethylhydrazinium iodide;

the strong base is selected from sodium methoxide or potassium tert-butoxide;

and the solvent is selected from dimethylsulphoxide N-methylpyrrolidone hexamethyl phosphoramide, dimethylformamide, dimethylacetamide or mixtures thereof.

15. A process to produce 1,3-diamino-2,4,6-trinitrobenzene (DATB) or 1,3,5-triamino-2,4,6,-trinitrobenzene (TATB), which process comprises:

(a) obtaining an aromatic compound as a starting mate, rial selected from:

(III)

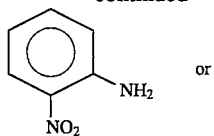

(IV)

mixtures thereof from commercial sources or by:

(i) reacting

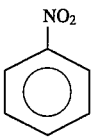

at a temperature of between about 0° and 50° C. for between about 0.1 and 24 hr with an amount effective of 1,1,1,-trialkylhydrazinium halide wherein alkyl is selected from methyl, ethyl, propyl, butyl, or benzyl, and halide is selected from chloride, bromide or iodide.

in the presence of a base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of dimethylsulphoxide, N-methylpyrrolidone, hexamethylphosphoramide, dimethylformamide, dimethylacetamide, or mixtures thereof, and isolating the product which are compounds III and/or IV;

(ii) or nitrating aniline using a mixture of nitric acid and sulfuric acid to produce compounds III and IV; or (iii) nitrating acetanilide using a mixture of nitric acid and sulfuric acid to produce 4-nitroacetanilide and nitrating further using a mixture of nitric acid and sulfuric acid to produce compound VI;

(b) reacting 2-nitroaniline, 4-nitroaniline or combinations thereof with a nitric acid, and sulfuric acid mixture under conditions to produce 2,4,6-trinitroaniline (VI);

(A) reacting at ambient pressure and a temperature of between about 0° and 50° C. for between about 0.1 and 24 hr a trinitro aromatic compound selected from:

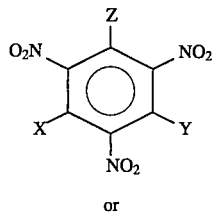

(V)

or

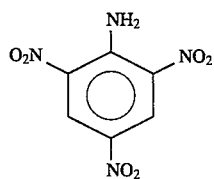

(VI)

wherein X, Y, and Z are each independently selected from the group consisting of —H and —NH₂, with the proviso that at least 1 of X, Y, and Z is hydrogen, with an effective amount of 1,1,1-trialkylhydrazinium halide wherein alkyl is selected from methyl, ethyl, propyl, butyl or benzyl, and halide is selected from chloride, bromide or iodide, in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (B) isolating the DATB or TATB produced.

16. The process of claim 11 wherein the reaction temperature is between about 10° and 30° C.

17. A process to produce mono or polyamino, mono or poly nitrobenzene, which process comprises:

(A) obtaining an aromatic compound as a starting material selected from the following structures:

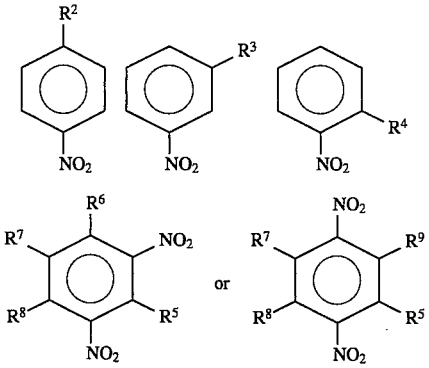

wherein $R^2$, $R^3$, and $R^4$ are each independently selected from —H, —CH₃, F, —C, —Br, —I, CN or OCH₃, and $R^5$–$R^9$ are each independently selected from —H, —CH₃, F, —Cl, —Br, —I, —CN or —OCH₃ or mixtures thereof, with the proviso that at least 1 of $R^5$–$R^9$ is H;

(B) reacting at ambient pressure and a temperature of between about 0° and 50° C. for between about 0.1 and 24 hr a nitro aromatic compound;

with an effective amount of 1,1-dialkyl-1,2-di-R-[(R= alkyl or aryl)] hydrazinium halide wherein dialkyl is selected from methyl, ethyl, propyl or butyl, R is selected from H, $C_1$–$C_{20}$ alkyl, or aryl, and halide is selected from chloride, bromide or iodide, in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (C) isolating the monoamino, diamino or triaminosubstituted nitroaromatic compound produced.

18. The process of claim 17 wherein the temperature is between about 10° and 30° C.;

the time is between about 0.1 and 24 hr;

the starting material is a substituted or unsubstituted mononitro or dinitro benzene;

R is hydrogen; and halide is iodide.

19. The process of claim 15 wherein in the starting material V where

X, Y and Z are independently selected from H or NHR; and the reaction temperature is between about 10° and 30° C.

20. The process of claim 19 wherein the solvent is not an alcohol and TATB is produced.

* * * * *